(12) United States Patent
Erbacher et al.

(10) Patent No.: US 8,143,229 B2
(45) Date of Patent: Mar. 27, 2012

(54) METHOD FOR PRODUCTION OF A TRANSFORMED CELL

(75) Inventors: Christoph Erbacher, Haan (DE); Ute Krüger, Solingen (DE)

(73) Assignee: Qiagen GmbH, Hilden (DE)

( * ) Notice: Subject to any disclaimer, the term of this patent is extended or adjusted under 35 U.S.C. 154(b) by 617 days.

(21) Appl. No.: 12/280,499

(22) PCT Filed: Feb. 21, 2007

(86) PCT No.: PCT/EP2007/051661
§ 371 (c)(1),
(2), (4) Date: Aug. 22, 2008

(87) PCT Pub. No.: WO2007/096382
PCT Pub. Date: Aug. 30, 2007

(65) Prior Publication Data
US 2009/0010871 A1 Jan. 8, 2009

(30) Foreign Application Priority Data

Feb. 23, 2006 (DE) .......................... 10 2006 008 701

(51) Int. Cl.
*A61K 48/00* (2006.01)
*A61K 31/00* (2006.01)
*A01N 61/00* (2006.01)

(52) U.S. Cl. ........................... 514/44 R; 514/1; 977/702

(58) Field of Classification Search .................. None
See application file for complete search history.

(56) References Cited

U.S. PATENT DOCUMENTS
2006/0147376 A1* 7/2006 Yu et al. .......................... 424/9.1
2007/0298006 A1* 12/2007 Tomalia et al. ............. 424/78.03

FOREIGN PATENT DOCUMENTS
EP 1 552 818 7/2005
WO WO 2004/078822 9/2004

OTHER PUBLICATIONS

Qu et al., "Adsorption Property and Mechanism of Polymeric Aza-Crown Ether Resin for Metallic Ions," (XP007904004) (Abstract) Database Caplus, Chemical Abstract Service, Columbus, Ohio, U.S. (1999).
Qu et al., "Adsorption Property and Mechanism of Polymeric Aza-Crown Ether Resin for Metallic Ions," Gaofenzi Cailiao Kexue Yu Gongcheng, Sichuan Daxue, Gaofenzi Yanjiusuo, CN, vol. 15, No. 2, pp. 151-154 (XP008088326) (1999).
Nguyen H. K. et al., "Evaluation of Polyether-Polyethyleneimine Graft Copolymers as Gene Transfer Agents," Gene Therapy, Macmillan Press Ltd., Basingstoke, GB, vol. 7, pp. 126-138 (2000) (XP002947334).
Banerjee P. et al., "Linear Polyethyleneimine Grafted to a Hyperbranched Poly(ethylene glycol)-like Core: A Copolymer for Gene Delivery," Bioconjugate Chemistry, 17:125-131 (2005) (XP007904002).

* cited by examiner

*Primary Examiner* — Robert M Kelly
(74) *Attorney, Agent, or Firm* — Occhiuti Rohlicek & Tsao LLP

(57) ABSTRACT

A method for incorporating a biomolecule into a cell including the steps: i) production of a complex from a biomolecule and a polymer which may be obtained by reaction of an amine monomer having at least two amine groups with an epoxide monomer having at least two epoxide groups and ii) incorporation of the biomolecule into a cell bx bringing the cell into contact with the complex. The invention further relates to the transformed cell obtained by said method, the use of a particular polymer for incorporation of a biomolecule into a cell, a kit for incorporation of a biomolecule into a cell, the use of said kit, a complex made from a biomolecule and a polymer, a therapeutic composition, the use of a complex of a biomolecule and a polymer for therapeutic treatment and a method for treatment of a disease by gene therapy.

6 Claims, 1 Drawing Sheet

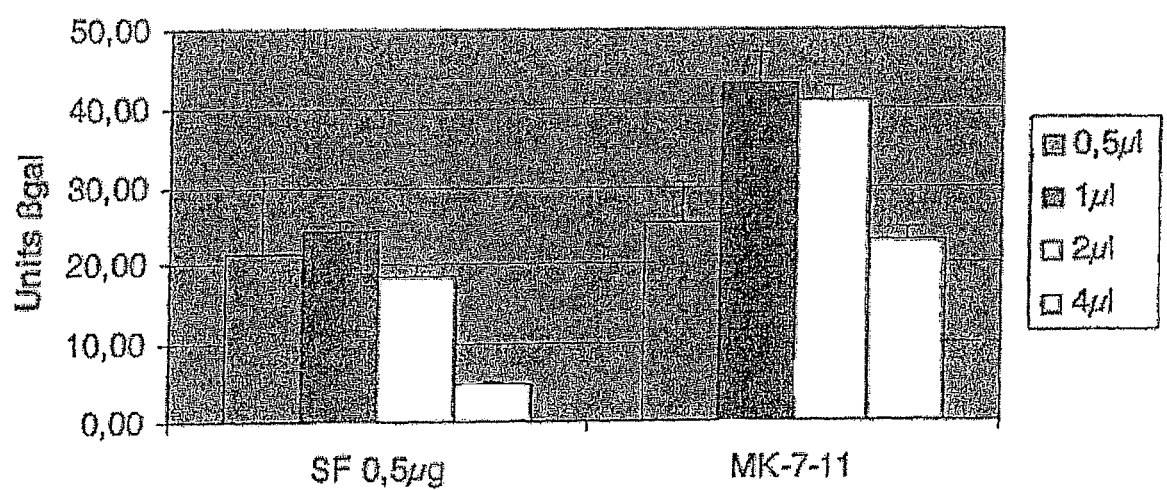

METHOD FOR PRODUCTION OF A TRANSFORMED CELL

CROSS-REFERENCE TO RELATED APPLICATIONS

This application is the National Stage of International Application No. PCT/EP2007/051661, filed on Feb. 21, 2007, which claims the priority of German Application No. 10 2006 008 701.1, filed on Feb. 23, 2006. The contents of both applications are hereby incorporated by reference in their entirety.

The present invention relates to a method for transferring a biomolecule into a cell, the use of a particular polymer for transferring a biomolecule into a cell, a kit for transferring a biomolecule into a cell, the use of said kit for transferring a biomolecule into a cell, a complex of a biomolecule and a polymer, a therapeutic composition, the use of a complex of a biomolecule and a polymer, a polymer for the treatment of a disease by means of gene therapy and a method for the treatment of a disease by means of gene therapy.

Numerous various methods are known in the prior art for incorporating foreign nucleic acids, in particular foreign DNA, into a cell (transformation or transfection). For transformation in vivo, essentially two methods are employed: virus-mediated gene transfer and transformation by means of cationic liposomes or cationic polymers, such as polyethylene imines, poly-L-lysine or poly-L-arginine. Viral vectors that are used include adenoviruses and retroviruses, which are able to transfect nonviral DNA into mitotically active cells. The cationic liposomes interact with the negatively charged phosphate backbone of DNA.

A suitable technique for transformation in vitro is calcium phosphate precipitation, in which, in a mixture of calcium chloride and sodium phosphate, the DNA to be transferred binds to the precipitating calcium phosphate. The precipitated crystals are added to the cell culture and are taken up by the cells by endocytosis. In addition to this chemical transformation technique, numerous physical in vitro transformation techniques are also known, such as microinjection, in which injection apparatus is used for directly injecting DNA into the cell nucleus or into the cell, electroporation, in which the cell membrane is made permeable to DNA by means of electric pulses, and the so-called particle gun technique, in which foreign DNA is shot into the cell with the aid of tiny metal spheres coated with the DNA.

A particular disadvantage of the in vitro transformation techniques described above is that the techniques are often very cell-specific. In calcium phosphate precipitation, the transformation process is moreover highly dependent on selection of the correct salt concentrations and requires experimental skill and experience from one type of cell to another. Even more importantly, however, the transformation techniques described in the prior art have the disadvantage that transformation reagents that possess an adequate transformation efficiency are often highly cytotoxic, whereas reagents that have little if any cytotoxic properties are often characterized by unsatisfactory transformation efficiency.

As an alternative, in order to overcome these disadvantages, cationic polymers are used for in vitro transformation or transfection of cells. For example, it is known that the complexing of DNA with polyethylene imine (PEI) can be used successfully for transporting genes into the cell (Boussif et al., 1995; Boussif et al., 1996; Abdallah et al., 1996). In this case gene transfer takes place by the complexes being bound randomly to cells and taken up. As well as polyethylene imines, also homopolymers of basic amino acids, such as poly-L-lysine, dendritic cationic polymers, such as polyamidoamines (PAMAMs), polyamides, polyallylamines, cationic methacrylates, chitosan or poly(D,L-lactide-co-glycolide) (PLGAs) are used as cationic polymers for transfection of cells. A review of cationic polymers that can be used for transfection of cells is offered for example by Holtorf and Mikos in "*Cationic and non-condensing polymer-based gene delivery*", Pharmaceutical Perspectives of Nucleic Acid-Based Therapeutics, 2002 (183), pages 367-387.

The disadvantage of these cationic polymers known from the prior art is either that they only have low transfection efficiency, or that although they are characterized by a satisfactory transfection efficiency, they are often highly cytotoxic. Moreover, with some of the polymers known from the prior art, in particular the dendritic polymers, the cost of synthesis is disproportionately high. For instance, it takes many weeks to synthesize a 42 kDa PAMAM dendrimer.

One aim of the present invention was to overcome the disadvantages arising from the prior art in the transformation of cells, in particular in vitro transformation.

A further aim of the present invention was to provide a method for the production of a transformed cell, said method being characterized by a high transformation efficiency. In addition, if at all possible the method should not require the use of cytotoxic auxiliaries.

Another aim of the present invention was to provide a method for the production of a transformed cell in which it should be possible for the auxiliaries used for transformation to be adapted, at the lowest possible cost of synthesis, to the peculiarities of the cell populations to be transformed and the particular transformation conditions. It should also be possible for the auxiliaries used to be produced as easily and inexpensively as possible.

A contribution to achievement of the aforesaid aims is provided by a method for transferring a biomolecule into a cell, which includes the steps:

i) preparation of a complex from a biomolecule, preferably a nucleic acid, and a polymer, which is obtainable by reaction of an amine monomer, having at least two amine groups, with an epoxide monomer, having at least two epoxide groups, and ii) transferring the biomolecule into a cell by contacting a cell with the complex.

It was found, entirely surprisingly, that by means of a polymer, which can be produced by a polyaddition reaction of a diamine with a diepoxide, biomolecules can be transferred into cells at high efficiency and with only slight cytotoxic stress.

In step i) of the method according to the invention, first a complex is prepared from a biomolecule and a polymer, which is obtainable by reaction of an amine monomer, having at least two amine groups, with an epoxide monomer, having at least two epoxide groups.

Preferably, the biomolecule that is used in step i) for the preparation of the complex, is a nucleic acid, so that the method according to the invention is suitable for the transformation of a cell. The term "transformation", as used here, describes quite generally the process of introducing biomolecules, in particular nucleic acids, preferably deoxyribonucleic acid (DNA), into any cells. It also comprises in particular the special case of transfection, in which foreign DNA is introduced into a cell culture cell. The term "transformation" comprises both the only temporary introduction of DNA, for example a gene, into the cell (transient transformation), and the permanent incorporation of the DNA in the genome of the cell (stable transformation).

The nucleic acid that is used in step i) for the preparation of the complex, and for which the term polynucleotide can also be used as a synonym, can be a ribonucleic acid (RNA), deoxyribonucleic acid (DNA), or also a mixed form, a deoxyribonucleic acid being especially preferred. In general it can be any type of polynucleotide that is an N-glycoside or C-glycoside of a purine or pyrimidine base or of a modified purine or pyrimidine base, thus can also contain bases that do not occur naturally. Apart from the base itself, the sugar residue can also be modified. It includes nucleic acids with modified linkage of the subunits, for instance phosphoro-thiolate or -amidate linkages. The nucleic acid can be single-, double- or multi-stranded, linear or circular. It can correspond to a molecule occurring in a cell, such as genomic DNA or messenger RNA (mRNA), or can be produced in vitro such as complementary DNA (cDNA), antisense RNA (aRNA), or synthetic nucleic acids. The nucleic acid can consist of a few subunits, at least two subunits, preferably eight or more subunits, such as oligonucleotides, several hundred subunits and up to several thousand subunits, such as certain expression vectors. Preferably the nucleic acid contains the coding information for a polypeptide in functional relationship with regulatory sequences, which permit expression of the polypeptide in the cell into which the nucleic acid is inserted.

Thus, in a preferred embodiment the nucleic acid is an expression vector. In another embodiment it is a pDNA (plasmid DNA), an siRNA, an siRNA-duplex, an siRNA-heteroduplex or an miRNA, with the term "siRNA" denoting ribonucleic acids with a length of about 22 nucleotides, which arise from cleavage of a double-stranded RNA (dsRNA) by the enzyme "Dicer" and are incorporated in the enzyme complex "RISC" (RNA-induced silencing complex). Synthetic siRNAs can also be used as biomolecules in step i).

In addition to nucleic acids, consideration may also be given to oligopeptides, proteins or lipids as biomolecules.

The polymer used in step i) can be obtained by reaction of an amine monomer, having at least two amine groups, with an epoxide monomer, having at least two epoxide groups.

According to a preferred embodiment of the method according to the invention, the amine monomer has at least two functional groups of structure I

I in which the residues $R^1$ within the functional group can be identical or different and represent a $C_1$ to $C_{20}$ hydrocarbon residue, especially preferably a $C_1$ to $C_{10}$ hydrocarbon residue and most preferably a $C_1$ to $C_5$ hydrocarbon residue, in particular a methyl residue, an ethyl residue, an n-propyl residue or an iso-propyl residue, a hydroxyfunctional $C_1$ to $C_{20}$ hydrocarbon residue, especially preferably a hydroxyfunctional $C_1$ to $C_{10}$ hydrocarbon residue and most preferably a hydroxyfunctional $C_1$ to $C_5$ hydrocarbon residue or alternatively a hydrogen atom. Furthermore, it is also preferable according to the invention for at least one of the residues $R^1$ within a functional group of structure I to be a hydrogen atom. The term "hydrocarbon residue" then comprises both residues that consist exclusively of carbon atoms and hydrogen atoms, and residues that, along with carbon atoms and hydrogen atoms, also include heteroatoms, in particular atoms from the halogen group (=halogenated hydrocarbons).

The functional amine group I can accordingly be a primary amine group, a secondary amine group or a tertiary amine group, and amine monomers with at least two primary amine groups (in this case both residues $R^1$ are a hydrogen atom) are the most preferred. Especially preferred residues $R^1$ are the ethyl group, the methyl group, the —CH$_2$CH$_2$OH— group and the hydrogen atom.

Furthermore, it is preferable according to the invention for the amine monomer to have the structure II

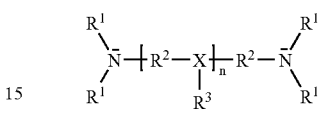

in which
X if present, is an oxygen atom or a nitrogen atom, especially preferably an oxygen atom or a nitrogen atom, and in the case of an oxygen atom the $R^3$ group on atom X is not present and the atoms X within an amine monomer can also be different,
$R^1$ within structure II can be identical or different and represents a $C_1$ to $C_{20}$ hydrocarbon residue, especially preferably a $C_1$ to $C_{10}$ hydrocarbon residue and most preferably a $C_1$ to $C_5$ hydrocarbon residue, in particular a methyl residue, an ethyl residue, an n-propyl residue or an iso-propyl residue, a hydroxyfunctional $C_1$ to $C_{20}$ hydrocarbon residue, especially preferably a hydroxyfunctional $C_1$ to $C_{10}$ hydrocarbon residue and most preferably a hydroxyfunctional $C_1$ to $C_5$ hydrocarbon residue or alternatively a hydrogen atom,
$R^2$ within structure II can be identical or different and represents a $C_1$ to $C_{20}$ alkylene group, especially preferably a $C_1$ to $C_{10}$ alkylene group and most preferably a $C_1$ to $C_6$ alkylene group or a $C_1$ to $C_{200}$ oxyalkylene group, especially preferably a $C_1$ to $C_{50}$ oxyalkylene group and most preferably a $C_2$ to $C_{10}$ oxyalkylene group, with the residues —CH$_2$CH$_2$—, —CH$_2$CH$_2$CH$_2$— and —CHCH$_3$CH$_2$— being especially preferred and —CH$_2$CH$_2$— most preferred as the residue $R^2$,
n when $R^2$ is an alkylene group, is an integer from the range from 0 to 6, especially preferably from 1 to 5, even more preferably from 1 to 3 and most preferably from 1 to 3, and when $R^2$ is an oxyalkylene group, it is an integer from the range from 0 to 100, especially preferably from 1 to 50, even more preferably from 2 to 25 and most preferably from 2 to 10, and
$R^3$ within structure II can be identical or different and represents a $C_1$ to $C_{20}$ hydrocarbon residue, especially preferably a $C_1$ to $C_{10}$ hydrocarbon residue and most preferably a $C_1$ to $C_5$ hydrocarbon residue, in particular a methyl residue, an ethyl residue, an n-propyl residue or an iso-propyl residue, a hydroxyfunctional $C_1$ to $C_{20}$ hydrocarbon residue, especially preferably a hydroxyfunctional $C_1$ to $C_{10}$ hydrocarbon residue and most preferably a hydroxyfunctional $C_1$ to $C_5$ hydrocarbon residue, a hydrogen atom or a residue of structure III

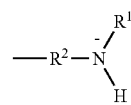
III with the residue —CH$_2$—CH$_2$—NR$^1$H, in particular with R$^1$=H and R$^2$=—CH$_2$CH$_2$—, being most preferred as residue R$^3$.

Amine monomers that are especially preferred according to the invention, which have structure II shown above, are selected from the group comprising the following monomers a to n:

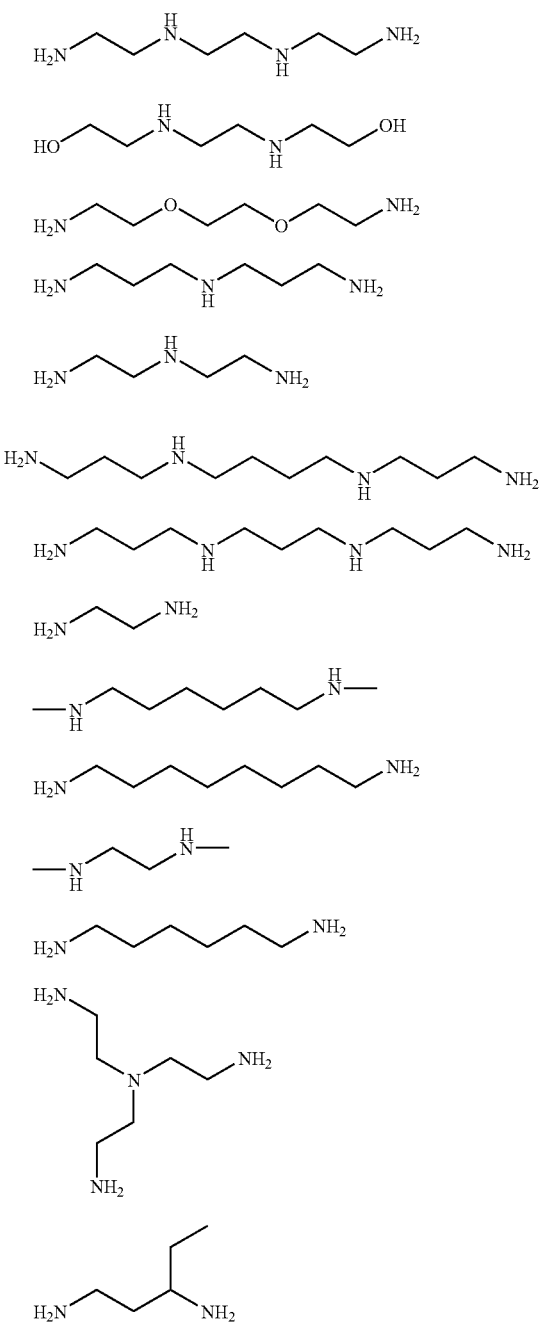

Apart from the amine monomers described above with structure II, according to another embodiment of the method according to the invention, for production of the polymers it is also possible to use amine monomers that include an optionally heteroatom-substituted, aromatic ring system, especially preferably an optionally heteroatom-substituted aromatic C$_6$ or C$_{10}$ ring system, to which at least two functional groups of structure I

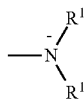

are bound, in which R$^1$ is as defined above.

"Aromatic ring system" preferably means any cyclic system of sp$^2$-hybridized carbon atoms, which satisfies Hückel's rule, where optionally also one or more halogen atoms, such as fluorine or chlorine (=halogenated aromatics), one or more alkyl groups, in particular methyl groups, or one or more hydroxyl groups can be bound to the carbon atoms.

The epoxide monomer used for preparation of the polymer is preferably an epoxide monomer that has at least two functional groups of structure IV

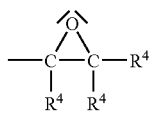

in which the residues R$^4$ within structure IV can be identical or different and represent a C$_1$ to C$_{20}$ hydrocarbon residue, especially preferably a C$_1$ to C$_{10}$ hydrocarbon residue and most preferably a C$_2$ to C$_5$ hydrocarbon residue, in particular a methyl residue, an ethyl residue, an n-propyl residue or an iso-propyl residue, a hydroxyfunctional C$_1$ to C$_{20}$ hydrocarbon residue, especially preferably a hydroxyfunctional C$_1$ to C$_{10}$ hydrocarbon residue and most preferably a hydroxyfunctional C$_2$ to C$_5$ hydrocarbon residue or a hydrogen atom, with a hydrogen atom being most preferred as residue R$^4$.

Especially preferred epoxide monomers according to the invention have structure V

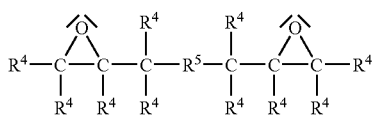

in which
R$^4$ is as defined above, and
R$^5$ if present,
represents a C$_1$ to C$_{20}$ alkylene group, especially preferably a C$_1$ to C$_{10}$ alkylene group and most preferably a C$_1$ to C$_6$ alkylene group, with —CH$_2$CH$_2$—, —CH$_2$CH$_2$CH$_2$— or —CHCH$_3$CH$_2$— being especially preferred as alkylene group and —CH$_2$CH$_2$— being most preferred, or is a group of structure VI

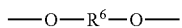

in which R$^6$
represents a C$_1$ to C$_{20}$ alkylene group, especially preferably a C$_1$ to C$_{10}$ alkylene group and most preferably a C$_1$ to C$_6$ alkylene group, where —CH₂CH₂—,
—CH₂CH₂CH₂—,
—CHCH₃CH₂—,
[—CH₂CH₂—]$_n$ with n=1 to 10,
[—CH₂CH₂CH₂—]$_n$ with n=1 to 10,
[—CHCH₃CH₂—]$_n$ with n=1 to 10, or a polyalkylene comprising ethylene and propylene units is especially preferred as alkylene group, or represents a $C_1$ to $C_{200}$ oxyalkylene group, especially preferably a $C_2$ to $C_{100}$ oxyalkylene group and most preferably a $C_2$ to $C_5$ oxyalkylene group, where
[—CH₂CH₂—O—]$_n$CH₂— with n=2 to 100,
[—CH₂CH₂CH₂—O—]$_n$CH₂CH₂CH₂— with n=2 to 100,
[—CHCH₃CH₂—O—]$_n$CHCH₃CH₂— with n=2 to 100, or a polyoxyalkylene comprising oxyethylene and oxypropylene units is especially preferred as oxyalkylene group.

Epoxide monomers especially preferred according to the invention, which have the structure V shown above, are selected from the group comprising the following monomers A to F:

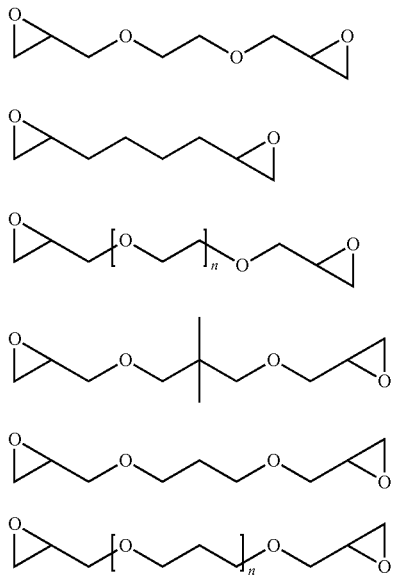

A
B
C
D
E
F

Polymers that are preferred according to the invention for use in step i) for the preparation of the complex are in particular those that can be obtained by reaction of the following monomeric components: aA, aB, aC, aD, aE, aF, bA, bB, bC, bD, bE, bF, cA, cB, cC, cD, cE, cF, dA, dB, dC, dD, dE, dF, eA, eB, eC, eD, eE, eF, fA, fB, fC, fD, fE, fF, gA, gB, gC, gD, gE, gF, hA, hB, hC, hD, hE, hF, iA, iB, iC, iD, iE, iF, jA, jB, jC, jD, jE, jF, kA, kB, kC, kD, kE, kF, lA, lB, lC, lD, lE, lF, mA, mB, mC, mD, mE, mF, nA, nB, nC, nD, nE, nF, oA, oB, oC, oD, oE, oF, qA, qB, qC, qD, qE, qF, rA, rB, rC, rD, rE, rF, sA, sB, sC, sD, sE, sF, tA, tB, tC, tD, tE, tF, uA, uB, uC, uD, uE, uF, vA, vB, vC, vD, vE, vF, wA, wB, wC, wD, wE and wF.

The reaction between the amine monomer and the epoxide monomer is an addition reaction, in which a polymer is formed, which, if an amine monomer with primary or secondary amine groups was used, has at least two structural units of structure VII

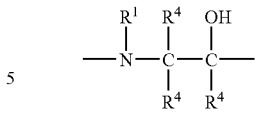

VII and in which $R^1$ and $R^4$ are as previously defined.

If, however, an amine monomer was used that included tertiary amine groups, a polymer is formed that has at least two structural units of structure VIII

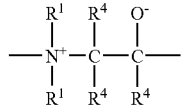

VIII in which $R^1$ and $R^4$ are also defined as described above.

Synthesis of the polymer, by polyaddition reaction from the amine monomer and the epoxide monomer can be carried out in the manner known by a person skilled in the art for this polymerization reaction. A person skilled in the art will determine the reaction conditions, in particular the type of solvent, the concentration of the educts (amine monomer and epoxide monomer), the reaction temperature and the reaction time in relation to the desired properties of the target product, in particular in relation to the desired molecular weight, by means of simple preliminary tests.

Usually the reaction is carried out by first dissolving or dispersing, preferably dissolving, both the amine monomer and the epoxide monomer in a suitable solvent, preferably using solvents in which both the amine monomer and the epoxide monomer are at least partially soluble. Examples of suitable solvents are water, alcohols, such as methanol, ethanol, 1-propanol, 2-propanol, n-butanol, tert.-butanol or isobutanol, ethers, ketones, hydrocarbons, halohydrocarbons, alkoxyalkanols, preferably alkoxypropanol, alkylpyrrolidones, for example N-methylpyrrolidone, dialkylsulfoxides, for example dimethylsulfoxide, or mixtures of at least two of these solvents.

At the beginning of adduct formation, the concentration of the individual monomers in the solvent is usually in a range from 1 to 10 000 mmol/l, especially preferably in a range from 10 to 5000 mmol/l, even more preferably 50 to 1000 mmol/l and most preferably 100 to 500 mmol/l.

Furthermore, if a polymer is to be prepared from amine monomers with the same structure and from epoxide monomers with the same structure, it may be advantageous to use the amine monomer and the epoxide monomer in a molar ratio of amine monomer to epoxide monomer from 2:1 to 1:2, especially preferably 1.5:1 to 1:1.5 and most preferably in a molar ratio of about 1:1.

The addition reaction is usually carried out at a temperature in a range from 10 to 200° C., especially preferably 20 to 150° C. and most preferably at 50 to 100° C., with the duration of the reaction as well as the temperature required for the reaction essentially being dependent on the reactivity of the monomers. Usually the addition reaction takes about 0.5 to 10 hours, especially preferably about 1 to 5 hours. When using an amine monomer with primary amine groups the reaction is usually carried out until primary amine groups can no longer be detected, whereas when using an amine monomer with secondary or tertiary amine groups the reaction is carried out until secondary or tertiary amine groups are no longer detectable.

According to a special embodiment of the method according to the invention, the polymer used in step i) for the preparation of the complex can be obtained by reaction of two structurally different amine monomers with an epoxide monomer. For instance, in this special embodiment of the method according to the invention it is possible to use a hydrophilic and a hydrophobic amine monomer.

When using two structurally different amine monomers, two procedures are conceivable for production of the polymer. On the one hand, both amine monomers can be dissolved or suspended together with the epoxide monomer in a suitable solvent, and in this case we get a random distribution of the monomers within the polymer, if both amine monomers have roughly the same reactivity with respect to the epoxide monomer. On the other hand, however, it is also possible first to react the one amine monomer with the epoxide monomer in excess, the molar ratio of amine monomer to epoxide monomer being at most 0.5:1, especially preferably at most 0.25:1 and most preferably at most 0.1:1. In this way polymers are obtained that have a reactive epoxide group at the end of the chain. After reacting the first amine monomer with the epoxide monomer, the polymers thus obtained are separated from the other components of the reaction mixture, in particular the epoxide monomers that are still present, and said separation can be carried out by a separation technique that is known by a person skilled in the art, for example extraction, distillation, crystallization or dialysis, especially preferably by dialysis. Then the polymer, provided it is now in the form of a pure substance after removal of the unreacted monomers, is dissolved again in a suitable solvent and is contacted with the second amine monomer, so that the second amine monomer now adds on to the terminal epoxide groups of the polymer.

It is of course also possible, in the same manner, to prepare a polymer from two structurally different epoxide monomers and one amine monomer. It is moreover also conceivable to use at least two, at least three, at least four or at least five structurally different amine monomers and/or to use at least two, at least three, at least four or at least five structurally different epoxide monomers.

On completion of the polyaddition reaction, we have a polymer dissolved or dispersed in the solvent used, along with unreacted amine and/or epoxide monomers. Before using the polymer for preparation of the complex in step i) of the method according to the invention it is therefore preferable to process the reaction mixture, in particular to separate the polymer from the other components of the reaction mixture. As separation technique, once again consideration may be given in particular to extraction, distillation, crystallization or dialysis, dialysis being especially preferred, because with dialysis the polymer is obtained directly dissolved or dispersed in a solvent. In addition, depending on the choice of dialysis membrane, dialysis provides selective isolation of a polymer of a specified size. In addition to separation of the polymer from the other components of the reaction mixture, it is also preferable to sterilize the polymer or in the case of dialysis, the composition of polymer and a solvent, and once again all sterilization methods known by a person skilled in the art can be employed, such as sterile filtration, γ-irradiation, irradiation with UV light or autoclaving, sterile filtration being the most preferred.

According to an especially preferred embodiment, the monomer is separated from the other components of the reaction mixture and the polymer is then sterilized, first diluting the reaction mixture with water at a volume ratio of reaction mixture to water in a range from 5:1 to 1:5, especially preferably 2:1 to 1:2 and most preferably of about 1:1 and the diluted reaction mixture thus obtained is then dialyzed by means of a dialysis membrane with a molecular weight cutoff of at most 10 kDa, especially preferably at most 5 kDa and most preferably at most 1 kDa preferably against an aqueous solvent, for example against demineralized water, against a physiological saline solution or against a nutrient medium. From the aqueous polymer solution obtained in this way, if it was dialyzed against water, the water is then separated preferably by freeze-drying, and in this case the pure polymer can be obtained. This polymer is then resuspended preferably in an aqueous medium, for example in demineralized water, physiological salt solution such as PBS or in a nutrient medium, and then sterile-filtered. The sterile aqueous polymer solution obtained in this way contains the polymer preferably at a concentration in a range from 0.1 to 500 mg/ml, especially preferably 0.5 to 100 mg/ml and most preferably from 1 to 10 mg/ml. It is also conceivable for the preferably aqueous polymer solution obtained directly following dialysis to be sterilized immediately. IMPORTANT: for in vitro use, the reagent must be sterile.

The molecular weight of the polymer used in step i), determined by mass spectrometry, is preferably in a range from 0.1 to 500 kDa, especially preferably 1 to 100 kDa and most preferably 10 to 50 kDa. In particular, by varying the reaction time, the concentration of the monomers, the solvent, the reaction temperature, the molar ratio of amine monomer to epoxide monomer and the cut-off value of the dialysis membrane, the average molecular weight of the polymer can be controlled in a simple manner and therefore the transformation efficiency can also be optimized for the particular transformation that is intended.

Furthermore, according to a special embodiment of the method according to the invention it may also be advantageous to modify the polymer chemically before or even after separation from the other components of the reaction mixture, modification preferably being carried out on the amino groups or hydroxyl groups present in the polymer. Modifications that are preferred according to the invention are modifications that promote the uptake of the polymer into a cell. Preferred modifications according to the invention include the attachment of a biotin group, as described for example in DE-A-100 16 881. The disclosure in this document with respect to the possibilities for targeted introduction of nucleic acids into cells by the attachment of effector groups to cationic polymers is hereby incorporated as reference and forms part of the disclosure of the present invention. In addition to biotin groups, the amine groups or the hydroxyl groups can also be modified with other effector groups, for instance with avidin or streptavidin, with ligands that bind to particular cell receptors, for instance with transferrin or with carbohydrates, in particular with galactosides, or with peptides with protein transduction domains. Furthermore, terminal diol groups can be formed in the polymer by treatment with glycidol, or negatively charged groups can be produced in the polymer by treatment with bromoacetic acid or salts thereof. Furthermore, the amino groups present in the polymer can be at least partially quaternized by treatment with alkylating agents, such as dimethylsulfate, methyl bromide, methyl tosylate or methyl mesylate. Transformation of the amino groups at least partially to arginine groups is also conceivable.

The complex produced in step i) from the biomolecule and the polymer is obtained by contacting the biomolecule with the polymer, the complex being constructed as a result of electrostatic interactions. Optionally the biomolecule, if it is a nucleic acid, prior to contacting with the polymer can first also be condensed by incubation with suitable enhancers, in particular with polypeptides, such as protamine sulfate from salmon sperm and the like. Contacting of the biomolecule with peptides in order to facilitate uptake into the cell is also conceivable. It is moreover conceivable for the polymer to be used in combination with another transformation agent, for example a liposomal or nonliposomal lipid or in a mixture with chemically different polymers, for introducing a biomolecule, in particular a nucleic acid, into a cell.

Preferably the biomolecule is contacted with the polymer in a weight ratio of biomolecule to polymer in a range from 10:1 to 1:50, especially preferably in a range from 1:1 to 1:30 and most preferably in a range from 1:2 to 1:20. A person skilled in the art can determine the optimized proportions of the mixture by routine experiments. Preferably, when the biomolecule is a nucleic acid, in the case of a positive charge excess the ratio of polymer to biomolecule is set so that the zeta potential is about +20 to +50 mV.

Contacting of the biomolecule with the polymer preferably takes place in an aqueous solution, for example a physiological saline solution, a buffer or a nutrient medium, contacting being carried out especially preferably at a pH value in a range from 5 to 8, especially preferably from 5.5 to 7.5 and at a temperature in a range from 4 to 40° C., especially preferably from 10 to 37° C. and most preferably from 15 to 25° C. Advantageously, this contacting is carried out by combining aqueous solutions of the components, and one or both of these solutions can also be buffered and optionally can contain other additives. Especially preferably, contacting is carried out in conditions in which the complex formed with the biomolecule does not dissociate at physiological saline concentration, which, for example when the biomolecule is a nucleic acid, can be determined easily by the ethidium bromide displacement assay (Plank et al. 1999).

In step ii) of the method according to the invention, the complex of the biomolecule and the polymer described above is contacted with a cell, obtaining a cell into which a biomolecule has been introduced, and said contacting can take place in vivo and in vitro, although in vitro treatment of the cells is especially preferred. It is then basically possible for the complex of biomolecule and polymer to be formed in the presence of the cells (and therefore steps i) and ii) are carried out simultaneously). It is conceivable and preferable, however, for complex formation to take place in absence of the cells to be treated, so that step ii) is carried out following step i).

In the case of in vitro treatment, cells or tissues can be incubated with the complex in a suitable environment, both prokaryotes and eukaryotes coming into consideration as cells. If culture cells are to be treated, the complex or the sterile aqueous solution containing the complex can be added to the culture medium. The method according to the invention is suitable both for cells growing in cell culture in suspension (suspension cells) and for cells growing while adhering to substrate surfaces (adherent cells).

For treatment in vivo, the complex or the sterile aqueous solution containing the complex can be applied in an animal or vegetable organism including humans. Application can be systemic or topical, and for animal organisms in particular parenteral, e.g. by intravenous, intraperitoneal, intramuscular, intradermal or subcutaneous injection, intravenous infusion, pulmonary, buccal, nasal, dermal or transdermal application. Other routes of application, e.g. oral/enteral application, are also possible under suitable conditions and with corresponding formulations. The complex or the sterile aqueous solution containing the complex can also be applied locally directly into a target tissue, for instance an organ or a tumor. For application in vivo, the complex should be in a pharmaceutically compatible form. For this, it can be combined with a pharmaceutically acceptable excipient. The formulation then depends on the method of application. For injection or infusion, the complex can for example be in isotonic saline solution or in an isotonic buffer such as PBS or Ringer's solution, for pulmonary administration for example in the form of a pharmaceutically compatible arosol. Solid formulations can also be chosen, depending on intended use, for example freeze-dried preparations, which can be reconstituted with water prior to administration. Suitable pharmaceutical excipients and formulations are known by a person skilled in the art, for example from Gennaro (Publ.), Remington: The Science and Practice of Pharmacy, 19th edition, 1995, Mack Publishing Co., Easton, Pa., USA. In this way, using an appropriate nucleic acid as biomolecule, the complex can be used as a medicinal product in gene therapy.

The dosage is selected by a person skilled in the art in relation to the nature of the disease, the patient's condition, the therapeutic approach and other factors. In general, when the biomolecule is a nucleic acid, for human use the amount of DNA administered will be in the range from 0.1 µg/kg to 100 µg/kg body weight, preferably 2.5 µg/kg to 10 µg/kg body weight.

A contribution to achievement of the aims stated at the beginning is moreover provided by a cell into which a biomolecule has been introduced by the method described above.

The use of the polymer described above, which is obtainable by reaction of the amine monomer, having at least two amino groups, with the epoxide monomer, having at least two epoxide groups, for transferring a biomolecule into a cell, preferably for the transformation of a cell, also makes a contribution to achievement of the aims stated at the beginning.

A further contribution to achievement of the aims stated at the beginning is also provided by a kit for transferring a biomolecule into a cell, preferably for the transformation of a cell, comprising (β1) the polymer described above, which is obtainable by the reaction of the amine monomer, having at least two amine groups, with the epoxide monomer, having at least two epoxide groups, and (β2) other kit components, in particular enhancers (for the purpose of condensation of the nucleic acid or for improved uptake), for example protamine sulfate from salmon sperm, additional buffers, such as PBS or physiological saline solution, reagents for controlling transformation efficiency and additional transformation reagents, for example liposomal or nonliposomal lipids or additional polymers.

Depending on the particular cell type to be transfected, a combination of polymer with lipids or liposomes or a mixture of various polymers may be useful. Thus, the use of a mixture generated on the basis of this patent application, but of chemically different polymers, could also be used.

A further contribution to achievement of the aims stated at the beginning is also provided by a complex of a biomolecule, preferably a nucleic acid, and the polymer described above, which is obtainable by reaction of an amine monomer, having at least two amine groups, with an epoxide monomer, having at least two epoxide groups. This complex can be obtained for example by contacting the biomolecule and the polymer in a suitable aqueous system, such as was described at the beginning in connection with the method according to the invention.

A contribution to achievement of the aims stated at the beginning is also provided by a therapeutic composition, containing the complex described above of a biomolecule, preferably a nucleic acid, and the polymer, which is obtainable by the reaction of the amine monomer, having at least two amine groups, with the epoxide monomer, having at least two epoxide groups. As well as this complex, the therapeutic composition can in particular also contain a pharmaceutically acceptable excipient, such as a physiological saline solution. Similarly, the use of the complex described above for production of such a pharmaceutical composition also makes a contribution to achievement of the aims stated at the beginning.

A contribution to achievement of the aims stated at the beginning is also provided by the polymer described in connection with the method according to the invention, which is obtainable by reaction of an amine monomer, having at least two amine groups, with an epoxide monomer, having at least two epoxide groups, for the therapeutic treatment of the human or animal body, preferably for the treatment of a disease by means of gene therapy.

Finally, the present invention also relates to a method for the treatment of a disease by means of gene therapy, comprising the steps:

I) removal of a cell from an organism,

II) transfer of a biomolecule into the cell that was removed, preferably transformation of the cell that was removed by the method according to the invention for transferring a biomolecule into a cell, and III) return of the cell into an organism.

As cells that may come into consideration for said gene therapy, in particular all cells can be used that are sufficiently resistant to withstand removal, introduction of the biomolecule, preferably transformation, and re-implantation from the or into the organism. Also, the cells should be as long-lived as possible, so that the organism can obtain sufficient benefit from the advantageous properties of the treated cell, for example from a protein secreted by a transformed cell. In particular, skin cells such as fibroblasts, liver cells, T-cells such as T-lymphocytes, or bone marrow cells are especially advantageous as cells.

The present invention will now be explained in more detail on the basis of nonlimiting examples.

FIG. 1 shows the transfection efficiency in the transfection of Huh-7 cells with a pCMVβ plasmid by the method according to the invention in comparison with conventional transfection techniques. The designation "MK-7-11" is the designation for the polymer obtained in the following example from triethylenetetramine and ethylene glycol diglycidyl ether.

EXAMPLE

Transformation of a Cell

Production of the Polymer

Triethylenetetramine (10 mmol) and ethylene glycol diglycidyl ether (10 mmol) are dissolved in 50 ml dimethylsulfoxide and the solution is conditioned in a round-bottom flask for 3 hours at 60° C. Then the reaction mixture was diluted with the same volume of demineralized water to double the volume, and dialyzed against demineralized water for 18 hours, changing the water three times (dialysis membrane with a molecular weight cutoff of 1 kDa). After dialysis, the sample was freeze-dried, obtaining a water-clear, viscous substance. This was dissolved in endotoxin-free, desalinated water, obtaining a polymer concentration of 3 mg/ml. The aqueous polymer solution thus obtained was sterilized by sterile filtration.

Cultivation of the Cells

The hepatoma cell line Huh-7 was plated out in a 96-well plate at a density of $2 \times 10^4$ cells/well in 100 µl DMEM medium per well. 24 hours after sowing the cells, transfection was carried out.

Formation of the Complex

To form the complex from nucleic acid and polymer, the amounts of DNA stated in Table 1 (pCMVβ plasmid, Clontech Laboratories), dissolved in DMEMS medium (0.01 µg/µl*) and the amounts stated in Table 1 of the aqueous, sterile solution of the polymer obtained from triethylenetetramine and ethylene glycol diglycidyl ether ("MK-7-11") were pipetted into the wells of a 96-well plate and were incubated for 10 minutes at room temperature. Transfection with the transfection reagent SuperFect® from the company Qiagen GmbH, Hilden, Germany, known from the prior art, was carried out as a control.

* Notes concerning the procedure: Complex formation between the DNA and the polymer was carried out in 50 µl culture medium without serum. The stated concentration relates to this volume. Following the incubation time of 10 minutes, 100 µl of culture medium with serum was added by pipette. The total volume (150 µl) was then added to the cells, from which the culture medium had been removed beforehand.

TABLE 1

| Complex | Amount of plasmid | Amount of polymer | Amount of Superfect ® |
|---|---|---|---|
| 1 | 0.5 µg | 0.5 µl | |
| 2 | 0.5 µg | 1 µl | |
| 3 | 0.5 µg | 2 µl | |
| 4 | 0.5 µg | 4 µl | |
| 5 | 0.5 µg | | 0.5 µl |
| 6 | 0.5 µg | | 1 µl |
| 7 | 0.5 µg | | 2 µl |
| 8 | 0.5 µg | | 4 µl |

Transfection of the Cells

For transfection, the complexes were added to the cells and incubated for 4 hours at 37° C., having changed the medium immediately beforehand. After the incubation time of 4 hours, the medium was changed, replacing the complex-containing solution with fresh cell culture medium. After incubating the cells with the complexes according to the invention or with the complexes of nucleic acid and SuperFect, on day 2 after transfection the cells were lysed with a lysis buffer (5 mM MgCl$_2$, 1% NP-40, 100 mM NaCl, 10 mM Tris/HCl, pH 7.4). The transfection efficiency was determined by a β-galactosidase assay with ONPG (2-nitrophenyl-β-D-galactopyranoside, Merck KGaA, Darmstadt, Germany) as substrate. The transfection efficiency (in units β-galactosidase per ml) is shown in FIG. 1.

It can be seen from FIG. 1 that by means of the method according to the invention, better transfection efficiencies can be achieved than with the transformation reagents known from the prior art.

The invention claimed is:

1. A method for transferring a biomolecule into a cell, comprising the steps:
    i) production of a complex from a biomolecule and a polymer, which is obtainable by reaction of an amine monomer with an epoxide monomer, and
    ii) transferring the biomolecule into a cell by contacting a cell with the complex, wherein the amine monomer is triethylenetetramine, the epoxide monomer is ethylene glycol diglycidyl ether, and the polymer includes both amine groups and hydroxyl groups.

2. The method as claimed in claim 1, wherein the preparation of the complex in step i) is carried out by contacting the polymer with the biomolecule at a pH value in a range from 6 to 8.

3. The method as claimed in claim 1, wherein the biomolecule is a deoxyribonucleic acid.

4. The method as claimed in claim 1, wherein the polymer has an average molecular weight of at least 0.1 kDa.

5. The method as claimed in claim 1, wherein the amine groups or the hydroxyl groups present in the polymer are modified chemically.

6. The method as claimed in claim 1, wherein the biomolecule is a nucleic acid.

* * * * *